United States Patent
Lu et al.

(10) Patent No.: US 6,331,346 B1
(45) Date of Patent: *Dec. 18, 2001

(54) INK RECEPTIVE COEXTRUDED FILM

(75) Inventors: Pang-Chia Lu, Pittsford; Michael Dale Cleckner, Honeoye, both of NY (US)

(73) Assignee: ExxonMobil Oil Corporation, Fairfax, VA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/151,129

(22) Filed: Sep. 10, 1998

(51) Int. Cl.$^7$ ........................................................ B32B 3/00
(52) U.S. Cl. ........................................................... 428/195
(58) Field of Search ................................... 428/195, 206, 428/207, 212, 515, 516

(56) References Cited

U.S. PATENT DOCUMENTS

| 4,853,290 | 8/1989 | Yanidis | 428/516 |
| 4,871,406 | 10/1989 | Griffith | 156/82 |
| 5,192,620 | 3/1993 | Chu et al. | 428/461 |
| 5,215,817 | 6/1993 | Chu | 428/330 |
| 5,225,306 | 7/1993 | Almog et al. | 430/115 |
| 5,276,492 | 1/1994 | Landa et al. | 355/277 |
| 5,346,769 | 9/1994 | Corley | 428/426 |
| 5,407,771 | 4/1995 | Landa et al. | 430/109 |
| 5,827,627 | * 10/1998 | Cleckner et al. | 430/18 |

* cited by examiner

Primary Examiner—Bruce H. Hess
Assistant Examiner—Michael E. Grendzynski
(74) Attorney, Agent, or Firm—Dennis P. Santini

(57) ABSTRACT

The invention discloses an ink-based-image-bearing substrate. This substrate includes a coextruded thermoplastic film having at least one layer made from a polymer derived from polypropylene and another layer made from an acidic functional group-bearing polymer. The layer which includes the polymer derived from the polypropylene is oriented in at least the machine direction. The layer which includes the acidic function group-bearing polymer is the print-receiving layer. The acidic functional group bearing-polymer is preferably ethylene-acrylic acid or ethylene-methacrylic acid, and the acidic functional group-bearing polymer-containing layer has a softening point in a range of 180° to 220° F. Liquid toner ink is electrostatically printed on the layer which includes the acidic functional group-bearing polymer. Additionally, the invention includes a method for providing the ink-based-image-bearing substrate.

5 Claims, No Drawings

INK RECEPTIVE COEXTRUDED FILM

BACKGROUND OF THE INVENTION

This invention relates to thermoplastic films which are capable of receiving ink derived from liquid toner, especially liquid toner employed in electrostatic printing.

Electrostatic printing is a very effective method of image transfer commonly used in photocopying and photo printing. Typically, in electrostatic printing, a potential electrostatic image is formed on an imaging surface carrying a uniform electrostatic charge. The uniform electrostatic charge can be created by exposing the surface to corona discharge. The uniform electrostatic charge is then selectively discharged by exposing it to a modulated beam of light which corresponds to an image formed from an original. The discharged surfaces form the background while the charged surfaces form the print image. The print image is developed by applying pigmented toner particles which adhere to the charged "print" portions of the surface. The pigment is subsequently transferred by various techniques to a copy sheet.

Dry toner is most commonly used in electrostatic printing. The quality and clarity of the image and image resolution, is related to the size of the toner particles. While it is thought that very fine particles will produce a finer image, there is a practical limitation on the size of toner particles which can be used. Dry toner particles must be of sufficient weight and size to be deposited onto the print surface without becoming airborne, which is thought to lead to machinery fouling and, possibly, environmental problems. Additionally, in fixing the image, the dry toner particles are fused onto the paper by exposure to very high temperatures, e.g. in excess of about 400° F. (204° C.). This energy requirement is a significant drawback.

Paper is widely used as the image receiving element in electrostatic imaging. It would be advantageous to use plastic as the receiving element. Among other advantages over paper, plastic is moisture resistant, flexible and heat sealable and plastic substrates can be either clear or opaque. However, the high temperatures necessary for imaging with the dry toners will melt plastic films and the liquid toners do not transfer well and adhere to uncoated plastic.

Plastic films which can receive printing inks have been disclosed; however, these films require specialized treatment to enable them to receive the dry toner. For example, a layer of plastic film used as a laminate for corrugated paperboards is disclosed in U.S. Pat. No. 4,871,406. The film is a thermoplastic co-extruded polymeric film, such as, polypropylene with ethylene acrylic acid. This film can receive printing inks only after being treated with a corona discharge device or a high velocity flame. Another example is U.S. Pat. No. 4,853,290 which discloses laminates of polypropylene film prepared by coextruding a polymer composition onto a polypropylene film. This polypropylene film requires corona treatment after printing on its surface.

Corona and flame treatments oxidize a plastic surface in order to enable the fixing of dry printing inks. Besides adding time, money and inconvenience to the production process, these treatments pose safety and environmental hazards. A corona treatment process generates toxic ozone so the atmosphere in the treating step must be contained and exhausted from the operating area. At high film speeds, a layer of air that contains ozone adheres to the film as it leaves the treating enclosure. This layer must be removed from the film by close-fitting baffles or a vacuum system. In some cases corona treatment requires special chambers and needs to be carried out off-line. Flame treatment entails impinging a flame directly onto a film surface as the film is moved across a cooling roll. The complexity of controlling the flame-treating process presents safety hazards.

To overcome these disadvantages, liquid toners have been developed in which the toner is dispersed in a solvent. The solvent is removed in the last printing step by the mechanism of the press. Because of the liquid medium, very fine dye particles can be employed without concern for the particles becoming airborne. Thus, copies of very high resolution can be made and high temperatures needed to fuse dry toners are not required. Liquid toners for electrostatic imaging are described in U.S. Pat. Nos. 5,225,306; 5,276,492; 5,346,769 and 5,407,771.

In order to enable plastic films to be printed upon with liquid toner, coatings can be applied which are able to receive inks (see U.S. Pat. No. 5,215,817). However, the use of coatings presents difficulties. The coating process adds time, money and inconvenience to the production process, and presents practical limitations.

Typical systems used for coating plastic films are the dispersion, solvent and extrusion coating processes.

The dispersion coating system is a multi-step, complex process that requires vigilant monitoring.

The dispersion coating process involves unwinding the film, applying the coating uniformly at the desired thickness, waiting for the coating to dry and rewinding the film into a uniform roll. Coating thickness should be measured across the film as part of the coating sequence. This can be done using radiation absorption. As the chemical nature of the coating more nearly approaches the substrate, this measurement becomes increasingly difficult.

The conditions of the dispersion coating process must be carefully monitored in order to ensure adequate coalescence of the coating. The dispersion coating polymer is dispersed in water often with a surfactant. Once the coating is applied, the water is evaporated. In order for a film to form, conditions need to be highly regulated. If evaporation occurs at room temperature, the dried polymer usually forms a fragile, uncoalesced coating. The particles need to make intimate contact with each other in order for coalescence to occur. Then diffusion and interpenetration of the polymer molecules must occur readily across the particle interfaces. The effectiveness of this diffusion depends on the mobility of the polymer molecules which in turn depends on the temperature of and the viscosity of the liquefying particle, which is a function of molecular weight. Therefore, a balance must be reached between a molecular weight low enough for coalescence but high enough for adequate toughness and flexibility of the coating film. Moreover, the surfactant used to create a stable dispersion can act as a barrier to interpenetration at the surface of the particles. Therefore an optimum must be found in the concentration of the surfactant.

The solvent coating system also entails a multi-step process. This process involves unwinding the film, applying the coating uniformly at the desired thickness, waiting for the coating to dry and rewinding the film into a uniform roll. The desired film thickness can be achieved by the use of radiation absorption.

An example of a solvent coating process for plastic films, which provides a surface that will receive liquid toners, is a polyamide solution sold under the name TOPAZ by Indigo Company.

In the solvent coating process, the coating polymer is dissolved in a solvent. The solvent is evaporated once the coating is applied leaving behind a coating film. However, as the coating develops it acts as a solvent barrier which makes it difficult to drive off the last traces of residual solvent. An additional disadvantage in the solvent coating process is that the solution is sensitive to ambient conditions. The solution is difficult to handle at low temperatures (it tends to lose solubility) and the coating absorbs atmospheric moisture which may make the film tacky even after drying. Among others, this can pose blocking problems.

Significantly, the polyamides used in the solvent coating process can present environmental hazards. Disposal of the solvent must be conducted in a proper manner. Moreover, recovery of solvent, which has become airborne, is complex.

In the extrusion coating process, the substrate film must be unwound, fed through a quench roll or between a quench roll and a nip roll to receive the falling polymer melt, and then the film must be rewound again onto a roll.

Additionally, practical considerations narrow down the field where the extrusion coating process can be utilized. Given the high temperature of the polymer melt, the substrate film must have high thermal stability. Additionally, there is a limitation on what can be used as a melt coating polymer. Very high melting polymers, polymers with low melt strength, and heat sensitive polymers are ruled out. Furthermore, coating thickness is limited at the low end to about 0.2 mil under the best conditions. (More comprehensively reviewed in *Plastic Films* by K. R. Osborn and W. A. Jenkins 1992, incorporated herein by reference.)

Thus, it is an object of the present invention to overcome difficulties presently encountered in the art by providing a coextruded thermoplastic film which is capable of receiving ink derived from liquid toner without the need of, among other things, coating(s) and/or post-extrusion or post-printing processes.

SUMMARY OF THE INVENTION

The present invention provides an ink-based-image-bearing substrate. This substrate includes a coextruded thermoplastic film having at least one layer made from a polymer derived from polypropylene and another layer made from a polymer bearing an acidic functional group. The layer which includes the polymer derived from the polypropylene is oriented in at least the machine direction. The layer which includes the polymer bearing an acidic functional group is the print-receiving layer. Liquid toner ink is electrostatically printed on the layer which includes the polymer bearing an acidic functional group. The polymer bearing an acidic functional group is preferably ethylene-acrylic acid or ethylene methacrylic acid. Additionally, the invention includes a method for providing the ink-based-image-bearing substrate.

The ethylene-acrylic acid copolymer layer of the film preferably has an acrylic acid content in the range of 1.0 to 18.0 wt %, and the most preferred range is from 2.0 to 6.0 wt %.

The ethylene-methacrylic acid copolymer layer of the film preferably has an methacrylic acid content in the range of 1.0 to 18.0 wt %, and the most preferred range is from 2.0 to 6.0 wt %.

Furthermore, the print-receiving layer has a softening point in a range of 180°–220° F., which is lower than the orientation temperature for oriented polypropylene.

It is an advantage of this invention that when a thermoplastic film has a layer made from a polymer bearing an acidic functional group, especially with an optimal acid content, liquid toner can be used in electrostatic imaging of the film without the difficulties presented by coating processes.

The application of coatings to thermoplastic films adds time, money and inconvenience to the production process. Coating systems are multi-step, complex processes requiring extensive physical manipulation of the substrate films. Such processes include unwinding the substrate film, applying the coating, allowing the coating to dry and rewinding the film into a uniform roll. Achieving the desired thickness for a coating may involve the use of radiation absorption.

Furthermore, the dispersion coating process requires vigilant monitoring of process conditions, including the temperature and viscosity of the liquefying particles.

The solvent-based coatings present the additional problems of environmental hazards pertaining to solvent disposal. Furthermore, solutions used in these solvent-based coatings are sensitive to ambient conditions, such as temperature and atmospheric moisture which further complicate the production process.

Extrusion coating systems further present limitations with respect to the substrate films and polymer melts that can be used.

DETAILED DESCRIPTION OF THE INVENTION

The present invention provides an ink-based-image-bearing substrate. This substrate includes a coextruded thermoplastic film having at least one layer made from a polymer derived from polypropylene and another layer made from a polymer bearing an acidic functional group. The layer which includes the polymer derived from polypropylene is oriented in at least the machine direction. The layer which includes the polymer bearing an acidic functional group does not undergo orientation since it has a lower melting point than the layer which includes the polymer derived from polypropylene. The layer which includes the polymer bearing an acidic functional group is the print-receiving layer. Liquid toner ink is electrostatically printed on this layer which includes the polymer bearing an acidic functional group. This ink-receiving layer should be substantially resistant to the hydrocarbon liquid carrier used in liquid toner. The polymer bearing the acidic functional group is preferably ethylene-acrylic acid or ethylene-methacrylic acid. These films do not require oxidation treatment or coating processes for electrostatic printing.

This invention significantly improves the known procedures by utilizing a layer which includes a polymer bearing an acidic functional group. A preferred range of acid content is from about 1.0 to about 18.0 wt %, and most preferably from about 2.0 to 6.0 wt %. The polymer bearing an acidic functional group is preferably ethylene-acrylic acid or ethylene-methacrylic acid. The ethylene-acrylic acid preferably has an acrylic acid content from a range of 1.0 to 18.0 wt %, and most preferably having an acrylic acid content of about 2.0 to 6.0 wt %. The ethylene-methacrylic acid preferably has a methacrylic acid content from a range of 1.0 to 18.0 wt %, and most preferably having a methacrylic acid content of about 2.0 to 6.0 wt %. The ethylene content of the copolymer can be from about 82.0 to 99.0 wt. %, preferably 94.0 to 98.0 wt % of ethylene, while from about 1 to 18.0 wt. % can be of acrylic acid or methacrylic acid.

Ethylene acid copolymers belong to a family of ethylene copolymers in which the polyethylene chain is modified by the presence of pendant carboxyl groups. These copolymers are characterized by good toughness and adhesion to a variety of metallic and nonmetallic substrates. Ethylene acid copolymers are produced by the high pressure free radical copolymerization of acrylic acid or methacrylic acid with ethylene to form ethylene acrylic acid or ethylene methacrylic acid. When ethylene is copolymerized with acrylic acid or methacrylic acid, the molecular structure is significantly altered by the random inclusion of bulky carboxylic acid groups along the backbone and side chains of the copolymer. The carboxyl groups are free to form bonds and interact with any polar substrate. The carboxyl groups disrupt the linearity of the polyethylene backbone and reduce the total crystallinity. A commercially available ethylene-acrylic acid copolymer is Primacor 4983 sold by Dow Chemical Co. The ethylene-acrylic acid is often supplied as a resin.

Polypropylenes commercially suitable for this invention include Fina 3371 (available from Fina Oil and Chemical Co. of Dallas, Tex.), Exxon 4612 and Exxon 4252 (available from Exxon Chemical Co. of Houston, Tex.) and Amoco 6361 (available from Amoco Chemical Co. of Chicago, Ill.).

The term "liquid toner" covers a composition in which toner particles are dispersed in a liquid base. Typically the liquid base is non-polar such as an aliphatic hydrocarbon fraction. Typical toners of this kind, and processes for using them in imaging, are described in U.S. Pat. Nos. 5,225,306; 5,276,492; 5,346,796 and 5,407,771. The coextruded films of this invention, surprisingly, are capable of receiving toner derived from these liquid toner compositions.

The ethylene-acrylic acid copolymer layer of the film has a softening point in a range of 180°–220° F., which is lower than the orientation temperature for oriented polypropylene. This feature allows for additional smoothing of the ethylene-acrylic acid surface which enhances the printability of the surface.

Optionally, the films of this invention can contain a relatively inert particulate filler additive. A filler which has found specific utility in the coextruded film of this invention is fumed silica. The fumed silica is composed of particles which are agglomerations of smaller particles and which have an average particle size of, for example, about 2 to 9 microns, preferably about 3 to 5 microns. Generally any finely divided inorganic solid materials such as silica is contemplated as a useful filler for purposes of the present coextruded film. These include talc, calcium carbonate, diatomaceous earth, calcium silicate, bentonite and clay. The total amount of filler typically ranges from about 0.1% to about 80%, specifically from about 0.3% to 7.0% based on the entire weight of the coextruded film. When a clear film is needed the particulate concentration will be relatively low, for example from about 0.1% to about 10%, specifically from about 0.3% to about 7.0%. The particulates are generally small in size, typically ranging from about 1 m to about 10 m specifically from about 3 m to about 7 m. Further examples of fillers include kaolin, silica, aluminum silicates, clay and talc. Pulp is also contemplated.

Preferred among the foregoing fillers are those that function as antiblock/slip agents. Silica is a specific example of a filler which is found to function in this manner.

Opacity enhancing particulates may also be employed. These are relatively inert substances. Calcium carbonate is extensively used in thermoplastics since it is relatively inexpensive and easy to use. It can be used in its natural form but "precipitated calcium carbonate," which is prepared by chemical processes, can be employed. Sometimes, particles of calcium carbonate are coated with a resin to reduce plasticizer absorption and this form can also be employed.

The filler can also include pigment-imparting particulates. Pigments contemplated are organic or inorganic substances with particle sizes which are rarely less than 1 micron in diameter. Typical pigments include carbon black and titanium dioxide. Calcium carbonate can also act as a pigment. Other pigments not to be excluded by this invention are metallic pigments such as particles of aluminum, copper, gold, bronze or zinc. These pigments are usually flake shaped particles which reflect light when incorporated into the coextruded film.

The fillers, including inert particulate slip/antiblock agents, opacifying agents, and/or pigments can be used in combination, depending upon the desired degree of translucency or opacity. Typically when the opacifying particulates and/or pigments are used, the concentration is less than about 70% of the total particulate concentration of the film, specifically about 20% to about 50% of the total particulate concentration of the film.

Further specific examples of particulates which may be employed in addition to those noted above include acetylene black, alpha cellulose, aluminum silicates, barium sulfate, calcium silicate, calcium sulphate, cellulose, clays, diatomite, glass flake, keratin, lignin, lithophone, mica, microballoons, molybdenum disulfide, nepheline syenite, paper, pulp, quartz, shell flour, talc, vermiculite and wood.

Additionally, the invention includes a method for providing the ink-based-image-bearing substrate. In a preferred method, a polypropylene resin and an ethylene-acrylic acid resin is coextruded to form a film with two layers. The film is then quenched by casting it onto a cooling drum. Upon reheating the film, the film is stretched about 3 to 7 times in the machine direction. Stretching allows for orientation of the polypropylene-containing layer. The ethylene-acrylic acid-containing layer does not orient during stretching due to it having a lower melting temperature than the polypropylene-containing layer. Next an image is formed on the ethylene-acrylic acid layer of the film with an electrostatic printing toner derived from a liquid toner composition.

What is claimed is:

1. An ink-based-image-bearing substrate comprising a coextruded polypropylene-containing layer which is oriented in at least the machine direction, an acidic functional group-bearing polymer-containing layer, wherein said acidic functional group-bearing polymer-containing layer has a softening point in a range of 180°–220° F.; and an ink image electrostatically printed on said acidic functional group-bearing polymer-containing layer by liquid toner.

2. The ink-based-image-bearing substrate according to claim 1, in which said acidic functional group-bearing polymer is ethylene-acrylic acid having an acrylic acid content is from about 2.0 wt % to about 6.0 wt %.

3. The ink-based-image-bearing substrate according to claim 1, in which said acidic functional group-bearing polymer is ethylene-methacrylic acid having a methacrylic acid content is from about 2.0 wt % to about 6.0 wt %.

4. The ink-based-image-bearing substrate according to claim 1, in which said acidic functional group-bearing polymer layer has a softening point which is lower than the polypropylene layer.

5. A method for providing the ink-based-image-bearing substrate of claim 1, which comprises assembling said layers followed by electrostatic printing.

* * * * *